United States Patent [19]

Schaeffer et al.

[11] 4,110,404

[45] Aug. 29, 1978

[54] HYDROCARBONYLATION

[75] Inventors: William D. Schaeffer, Pomona; Frank B. Booth, Placentia, both of Calif.

[73] Assignee: Celanese Corporation, New York, N.Y.

[21] Appl. No.: 840,815

[22] Filed: Jul. 10, 1969

Related U.S. Application Data

[63] Continuation-in-part of Ser. No. 518,562, Jan. 4, 1966, abandoned.

[51] Int. Cl.$^2$ ............................................. C07C 45/08
[52] U.S. Cl. ............................................. 260/604 HF
[58] Field of Search ................................. 260/604 HF

[56] References Cited

U.S. PATENT DOCUMENTS

| | | | |
|---|---|---|---|
| 3,278,612 | 10/1966 | Greene | 260/604 HF |
| 3,511,880 | 5/1970 | Booth | 260/604 HF |
| 3,594,425 | 7/1966 | Brader et al. | 260/604 HF |

FOREIGN PATENT DOCUMENTS

| | | | |
|---|---|---|---|
| 41,653 | 1/1966 | Japan | 260/604 HF |

Primary Examiner—James O. Thomas, Jr.
Assistant Examiner—W. B. Lone
Attorney, Agent, or Firm—Kenneth A. Genoni

[57] ABSTRACT

An ethylenically unsaturated hydrocarbon is hydroformylated to an aldehyde having one more carbon than the unsaturated hydrocarbon by contacting the unsaturated hydrocarbon, carbon monoxide and hydrogen in the presence of a reaction medium comprising a Group VIII noble metal and a bicyclo or tricyclo(heterocyclo) saturated amine having 2 to 10 carbons, 1 to 4 nitrogens and at least one nitrogen in a bridgehead position. Liquid phase contacting is employed with the catalyst dispersed in a liquid phase at temperatures from 50° to about 200° C. and pressures from 1 to 300 atmospheres. A typical reaction comprises contacting ethylene, carbon monoxide and hydrogen at a temperature of about 88° C. and a pressure of 50 atmospheres with an inert liquid reaction medium containing rhodium chloride and triethylenediamine. Preferably the reaction medium also contains a biphyllic ligand which is a trivalent phosphorus, antimony or arsenic organic compound. The presence of the heterocyclo saturated amine has been found to increase the yield of the aldehyde without increasing the yield of alcohol and/or dimerized products.

2 Claims, No Drawings

HYDROCARBONYLATION

DESCRIPTION OF THE INVENTION

This application is a continuation-in-part of application Ser. No. 518,562, filed Jan. 4, 1966, now abandoned.

This invention relates to the preparation of carbonyl compounds from ethylenically unsaturated hydrocarbons and in particular relates to a method for the hydrocarbonylation of olefins to aldehydes having one more carbon atom per molecule than the hydrocarbon.

The hydrocarbonylation of ethylenically unsaturated hydrocarbons to carbonylated products such a aldehydes, alcohols and acetals is well known in the art as illustrated in U.S. Pat. Nos. 2,694,735 and 3,239,566. Furthermore, U.S. Pat. No. 3,278,612 to Greene demonstrates that the addition of an alkyl amine to a tertiary alcohol reaction medium containing a cobalt carbonyl catalyst increases the yield of 2-ethylhexanol, an alcohol dimer, from propylene. The Greene process is useful where it is desirable to effect dimerization and hydrogenation to produce a dimer alcohol from an olefin, however, the addition of the alkyl amine in Greene does not increase the yield of an aldehyde having one more carbon than the reactant olefin.

It is an object of the invention to improve the yields of aldehydes in a hydrocarbonylation process.

It is another object of the invention to increase the yield of an aldehyde having one more carbon than the reactant ethylenically unsaturated compound without increasing dimerization and/or the yield of alcohol.

A still further object of the invention is to enable a hydrocarbonylation reaction to be conducted in the absence of a primary or secondary alcohol.

Other related objects will be apparent from the following description of the invention.

The invention comprises contacting an ethylenically unsaturated hydrocarbon with carbon monoxide and hydrogen in the presence of a liquid reaction medium containing a catalyst comprising a Group VIII noble metal and a bicyclo or tricyclo(heterocyclo) saturated amine having 2 to about 10 carbons and at least one nitrogen in a bridgehead position at a temperature between 50° and 200° C. sufficient to cause carbonylation of the ethylenically unsaturated compound. In a preferred embodiment, the reaction is also conducted in the presence of a third catalyst component which serves to stabilize the catalyst in an active state and which serves to increase the rate of reaction. This optional component of the catalyst comprises a biphyllic ligand of phosphorus, arsenic or antimony, to be defined hereinafter.

With the aforementioned catalyst which is described in greater detail hereinafter, the carbonylation of the ethylenically unsaturated hydrocarbon proceeds rapidly at relatively mild conditions including temperatures from about 50° to about 200° C. and pressures of from 1 to about 300 atmospheres with ratios of hydrogen to carbon monoxide in the reactants from 10:1 to about 1:10. The use of the aforementioned bicyclo or tricyclo (heterocyclo)amine greatly promotes the reaction and permits use of reaction solvents which are substantially non-reactive with the carbonyl products in contrast to much of the prior art on carbonylation which employs secondary or primary alcohols as the reaction medium which react with the aldehydes to form acetals. We have also discovered tht the combination of a Group VIII noble metal with the heterocyclo amine cocatalyst or promoter influences the product distribution and favors the production of the aldehydes to the substantial exclusion of alcohols. Specifically, we have found that less than 10 weight percent, preferably less than 5 percent, of the carbonylated product is comprised of alcohols, and less than 10 percent, preferably less than 5 percent, of the product is comprised of dimerization products, i.e., products having two or more carbons than the reactant unsaturated compound. This of course is a highly desired result because the aldehyde in many instances is the desired product. We have also found that the preferred catalyst has a high selectivity for production of the straight-chain aldehydes and that this selectivity can be greatly increased by use of limited concentration of carbon monoxide and/or by the addition of limited amounts of water to the reactants.

The compound carbonylated in accordance with our invention can comprise any ethylenically unsaturated hydrocarbon having from about 2 to about 25 carbons; preferably from 2 to about 18 carbons. This unsaturated hydrocarbon can in general be any of the following:

(1) ethylene and substituted ethylenes such as:

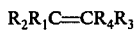

wherein $R_1$, $R_2$, $R_3$ and $R_4$ are hydrogen, alkyl, cycloalkyl, cycloalkylalkyl, aryl, alkaryl or araklyl which are inert and do not interfere with the reactivity of the olefinic group.

(2) cycloalkenes and substituted cycloalkenes such as:

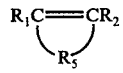

wherein $R_1$ and $R_2$ are as previously mentioned and $R_5$ is an alkylene or isoalkylene group having from 2 to about 6 carbons. Preferably $R_1$, $R_2$, $R_3$ and $R_4$ are hydrogen or alkyl, or monocyclic cycloalkyl, aryl, or araalkyl having 1 to 10 carbons.

Preferably the unsaturated hydrocarbon is an olefin. Examples of useful olefins are ethylene, propylene, butene-1, butene-2, pentene-2, 2-methylbutene-1, hexene-1, 3-ethylhexene-1, octene-3, 2-propylhexene-1, decene-2, 4,4-dimethylnonene-1, dodecene-1, 6-propyldecene-1, tetradecene-5, 7-amyldecene-3, hexadecene-1, 4-ethyltridecene-2, octadecene-1, 5,5-dipropyldodecene-3, eicosene-7, etc. Preferably the olefin is an alpha olefin, i.e., an olefin having a terminally unsaturated carbon, e.g., 5,5-dipropyldodecene-1. Choice of the particular olefin depends of course on the desired product. Intermediates for detergent synthesis can be prepared by reaction of alpha olefins having from 12 to about 18 carbons. Intermediates useful to prepare polymer plasticizers can be obtained by use of alpha olefins having from about 5 to 13 carbons.

Examples of other ethylenically unsaturated hydrocarbons which can be carbonylated are vinyl cyclohexane, allyl cyclohexane, styrene, p-methyl styrene, alpha methyl styrene, beta methyl styrene, p-vinyl cumene, beta vinyl naphthalene, 1,2-diphenyl ethylene, allyl benzene, 6-phenylhexene-1, 1,3-diphenylbutene-1, 3-benzoheptene-3, o-vinyl p-xylene, cyclobutene, cyclopentene, cyclohexene, methylcyclohexene, amylcyclopentene, cycloheptene, cyclooctene, cyclodecene, 3- phenyldodecene-1, 4-tolyl-3-ethyloctadecene-1, 3-butyl, 4-benzyldecene-2, etc.

The reaction is performed under liquid phase conditions and when the ethylenically unsaturated hydrocarbon is a liquid at the reaction conditions this material can be used in excess, e.g., 3–100 times that stoichiometrically required, to provide the liquid reaction medium. If desired, however, any suitable organic liquid can be employed as a reaction solvent, preferably organic solvents which are inert to the reaction conditions, the reactants, the catalyst and the products. Examples of suitable solvents which can be used in accordance with our invention include hydrocarbons such as the aromatics, aliphatics or alicyclic hydrocarbons, and ethers, esters and ketones, etc.

Examples of suitable hydrocarbons that can be employed in the solvents include aromatic hydrocarbons such as benzene, toluene, xylene, ethylbenzene, tetralin, etc.; aliphatic hydrocarbons such as butane, pentane, isopentane, hexane, siohexane, heptane, octane, isooctane, naphtha, gasoline, kerosene, mineral oil, etc.; alicyclic hydrocarbons, e.g., cyclopentane, cyclohexane, methylcyclopentane, decalin, indane, etc.

Various alkyl and aryl ketones can also be employed as the reaction solvent, e.g., acetone, methylethyl ketone, diethyl ketone, diisopropyl ketone, ethyl-n-butyl ketone, methyl-n-amyl ketone, cyclohexanone, di-isobutyl ketone, etc.

Ethers can also be employed as the reaction solvent, e.g., diisopropyl ether, di-n-butyl ether, ethylene glycol diisobutyl ether, methyl o-tolyl ether, ethylene glycol dibutyl ether, diisoamyl ether, methyl p-tolyl ether, methyl m-tolyl ether, dichloroethyl ether, ethylene glycol diisoamyl ether, diethylene glycol diethyl ether, ethylbenzyl ether, diethylene glycol diethyl ether, diethylene glycol dimethyl ether, ethylene glycol dibutyl ether, ethylene glycol diphenyl ether, triethylene glycol diethyl ether, diethylene glycol di-n-hexyl ether, tetraethylene glycol dibutyl ether, etc.

Various esters can also be employed as the solvent, e.g., ethyl formate, methyl acetate, ethyl acetate, n-propyl formate, isopropyl acetate, ethyl propionate, n-propyl acetate, sec-butyl acetate, isobutyl acetate, ethyl n-butyrate, n-butyl acetate, sioamyl acetate, n-amyl acetate, ethyl formate, ethylene glycol diacetate, glycol diformate, cyclohexyl acetate, furfuryl acetate, isoamyl n-butyrate, diethyl oxalate, isoamyl isovalerate, methyl benzoate, diethyl malonate, valerolactone, ethyl benzoate, methyl salicylate, n-propyl benzoate, n-dibutyl oxalate, n-butyl benzoate, diisoamyl phthalate, dimethyl phthalate, diethyl phthalate, benzyl benzoate, n-dibutyl phthalate, etc. A preferred class of ester solvents includes the alkyl lactones having 4 to 20 carbons, e.g., butyralactone, valerolactone and their derivatives having lower ($C_1$–$C_5$) alkyl substituents.

Alcohols can also be employed as a reaction solvent. Preferably tertiary alcohols are employed since these materials are substantially non-reactive under the reaction conditions. Primary and secondary alcohols can be employed but are less preferred since these materials can react with aldehyde compounds under the reaction conditions to produce acetals. While in some instances these may be desired products, it is generally desirable to produce the carbonyl compound or alcohol directly without the formation of the acetal. It is of course apparent, if desired, that the acetal can be hydrolyzed to obtain the aldehyde. Examples of alcohols that can be employed as solvents include the saturated aliphatic and alicyclic having 1 to 25 carbons such as methanol, ethanol, isopropanol, butanol, 5-butanol, 5-amyl alcohol, hexanol, cyclohexanol, etc. Preferably the alcohol is a tertiary saturated aliphatic alcohol having 3 to 15 carbons.

As indicated above, the reaction medium contains a Group VIII noble metal and a bi or tri (heterocyclo) saturated amine having 2 to 10 carbons, preferably 4 to 8 carbons and having 1 to 4 nitrogens, preferably 1 to 2 nitrogens and having at least one nitrogen in a bridgehead position. The exact identity of the reaction medium is not known with certainty since in the presence of the carbon monoxide, ethylenically unsaturated hydrocarbon and amine, complexes and carbonyls of the Group VIII noble metal can be readily formed. This is particularly true in regard to the preferred reaction medium hereafter described which also contains a biphyllic ligand.

The Group VIII noble metal can be of the palladium subgroup or the platinum subgroup, i.e., palladium, rhodium, or ruthenium or platinum, osmium or iridium. While catalyst containing any of these metals are active for the reaction, we prefer to employ rhodium or iridium, preferably rhodium because of their demonstrated greater activity, particularly at the relatively mild reaction conditions employed for the reaction. A catalytic quantity of the Group VIII noble metal containing catalyst is used. This is generally an amount sufficient to provide a concentration of the Group VIII noble metal which is between about 0.002 and about 2.0 weight percent, preferably 0.002 and about 0.5 percent of the liquid reaction medium. The Group VIII noble metal can be added to the reaction medium as a soluble salt, a carbonyl compound or chelate, and preferably as a halide, e.g., chloride, bromide or iodide. Examples of suitable salts are the nitrates and halides of the metals such as palladium chloride, palladium nitrate, rhodium acetate, ruthenium bromide, osmium fluoride, palladium chloride, etc. Examples of the suitable chelates are palladium acetyl acetonate and complexes of the platinum group metal ions with such conventional chelating agents as ethylenediamine tetraacetic acid and its alkali metal salts, citric acid, etc. The carbonyl of the Group VIII noble metal can be prepared externally and introduced into the reaction medium; preferably, however, the carbonyl compound is produced in situ by the addition of the aforementioned soluble salt or chelates of the Group VIII noble metal and introduction of the carbon monoxide during the reaction form the active carbonyl complex.

The cocatalyst or promoter employed with the aforementioned Group VIII noble metal is a bicyclo or tricyclo (heterocyclo) saturated amine having at least one nitrogen in a bridgehead position. The term "bridgehead position" is well established in chemical nomenclature to identify the position of an atom which is common to at least two of the rings of the polycyclic compound. Preferably the amine is an atom-bridged system, i.e., atoms, generally methylene carbons, form the bridge or link in the molecule rather than a simple valence bonding. It is the location of a nitrogen in the bridgehead position of a lower heterocyclo saturated amine which is believed to effect an improvement in aldehyde yields since other organic amines have not similarly improved the process as evidenced by the aforementioned Greene patent. The amine is used in catalytic amounts, e.g., from about 0.001 to about 10 weight percent; preferably from about 0.05 to 5 weight percent of the liquid reaction medium. In general, amines having from 2 to about 10 carbons, preferably 4 to 8 carbons and from 1 to about 4 nitrogens, preferably 1 to 2 nitrogens can be employed for this purpose. Particularly preferred are the bicyclo amines having 4 to 8 carbons and 1 to 2 nitrogens. The following is a listing of representative amines useful in our invention: 1,2,4-triazabicyclo(1.1.1)pentane; 1,5,6-triazabicyclo(2.1.1) hexane; 5-oxa-1,6-diazabicyclo(2.1.1)hexane; 5-thia-1,6-diazabicyclo(2.1.1)hexane; 2-oxa-1,5,6-triazabicyclo(2.1.1) hexane; 1,2,5,6-tetrazabicyclo(2.1.1)hexane; 5-oxa-1,2,3,6-tetrazabicyclo (2.1.1)hexane; 1-azabicyclo(3.3.1)heptane; 1-azabicyclo(2.2.1) heptane; 2-oxa-1-azabicyclo(2.2.1)heptane; 1,4-diazabicyclo(2.2.1) heptane; 7-oxa-1-azabicyclo(2.2.1)heptane; 7-thia-1-azabicyclo (2.2.1) heptane; 1,7-diazabicyclo(2.2.1)heptane; 1,3,5-triazabicyclo(2.2.1)heptane; 1-azabicyclo(3.2.1)octane; 1,5-diazatricyclo(4.2.1)decane; 1,7-diazatricyclo(3.3.1.2)undecane; 7-oxa-1-azabicyclo(3.2.1)octane; 1,7-diazabicyclo(3.2.1) octane; 3-thia-1, 7-diazabicyclo(3.2.1) octane; 1,3,6,8-tetrazatricyclo(6.2.1.1) dodecane; 2,8-diazatricyclo(7.3.1.1) tetradecane; 1-azabicyclo (3.3.1)nonene, also known as 1-isogranatinine and the oxo, hydroxy and lower alkyl derivatives thereof; 1-azabicyclo(2.2.2)octane also known as quinuclidine as well as the halo, oxo, hydroxy and lower alkyl derivatives thereof; 1-azatricyclo(3.3.1.1)decane; 1,3-diazabicyclo(2.2.2)octane; 1,3-diazabicyclo(3.3.1)nonene; 1,6-diazatricyclo(5.3.1.1)dodecane; 2-oxa-1-azabicyclo(2.2.2) octane; 4,6,10-trioxa-1-azatricyclo(3.3.1.1) decane; 1,5-diazabicyclo(3.3.1)nonene; 1,2,5,8-tetrazatricyclo(5.3.1.1)dodecane; 1,4-diazabicyclo(2.2.2)octane also known as triethylene diamine and its oxo, hydroxy, halo and lowerealkyl derivatives thereof; 1,3-diazatricyclo(3.3.1.1)decane also known as 1,3-diazaadamantane; 1,3,5-triazatricyclo(3.3.1)decane; 1,3,5,7-tetrazabicyclo(3.3.1) nonene also known as pentamethylene tetramine; 1,3,5,7-tetrazatricyclo(3.3.1.1)-decane also known as hexamethylene tetramine; 2-oxa-1,3,4-triazabicyclo(3.3.1)nonene; 1-azabicyclo(4.3.1)-decane; 1-azabicyclo(3.2.2)nonene; 1,5-diazabicyclo(3.2.2)nonene; 1,3,5,7-tetrazabicyclo(3.3.2)decane; 1,5-diazabicyclo(3.3.3) undecane; etc.

Of the aforementioned amines, the most common and widely known compound is triethylene diamine and this material as well as it oxo, hydroxy, halo and lower $C_1-C_5$ alkyl derivatives, preferably the alkyl derivatives, comprises the preferred cocatalyst for use in my process. And, in general, the hydrocarbon amines, i.e., those containing only carbon, hydrogen and nitrogen are preferred over those containing oxo, hydroxy and halo groups.

In a preferred embodiment the catalyst also comprises a third component which is a biphyllic ligand, i.e., a compound having an element with a pair of electrons capable of forming a coordinate bond with a metal atom and simultaneously having the ability to accept the electron from the metal, thereby imparting additional stability to the resulting complex. Biphyllic ligands can comprise organic compounds having at least about 3 carbons and containing arsenic, atimony or phosphorus in a trivalent state. Of these, the phosphorus compounds, i.e., the phosphines, are preferred; however, the arsines and stibines can also be employed. In general these biphyllic ligands have the following structure:

or the following structure:

wherein E is a trivalent atom selected from the class consisting of phosphorus, arsenic and atimony, and wherein R is a member of the class consisting of hydrogen, alkyl from 1 to 10 carbon atoms, monocyclic aryl, aralkyl or alkaryl from 6 to 10 carbons and cycloalkyl, alkylcycloalkyl or cycloalkylalkyl from 4 to 10 carbons and halo and alkoxy substitution products thereof; and wherein R' is alkylene having from 2 to about 8 carbons.

Preferably, at least one R group is aryl or alkaryl, e.g., phenyl, tolyl, xylyl, etc., preferably two and most preferably all three R groups are aryl or alkaryl.

Examples of suitable biphyllic ligands having the aforementioned structure and useful in my invention to stabilize the catalyst composition are the following: trimethyl phosphine, triethyl arsine, triisopropyl stibine, diethyl chloro phosphine, triaminobutyl arsine, ethyldiisopropyl stibine, tricyclohexyl phosphine, triphenyl phosphine, tri(o-tolyl)phosphine, phenyldiisopropyl phosphine, phenyl diamyl phosphine, diphenylethyl phosphine, chlorodixylyl phosphine, chlorodiphenyl phosphine, tris (diethylaminomethyl)phosphine, ethylene bis(diphenyl phosphine), hexamethylene bis(diisopropyl arsine), pentamethylene bis(diethylstibine), etc. Of the aforementioned, the aryl or alkaryl phosphines, preferably the triaryl or triaralkyl phosphines are preferred because of their demonstrated greater activity for stabilization of catalysts.

The reaction is performed under relatively mild conditions including temperatures from about 50° to about 200° C.; preferably from about 70° to about 150° C. most preferably 70° to about 120° C. In embodiments wherein the more active rhodium or iridium metals are utilized, temperatures as low as 50° to 95° C. may be employed. Sufficient pressure is used to maintain the reaction medium in liquid phase. Although atmospheric pressure can be used, the rate of reaction is increased by superatmospheric pressures and, therefore, pressures from about 5 to about 300 atmospheres absolute and preferably from about 10 to about 100 atmospheres are used. The ratio of the reactants can be widely varied if desired, e.g., the molecular ratio of hydrogen to carbon monoxide can be varied from about 1:10 to about 10:1. The preceding conditions are maintained by conventional means and since the reaction is exothermic, the temperature can be maintained by suitable cooling of all or a portion of the reaction zone contents. The pressure can be maintained by the pressure of the gases supplied to the reaction zone. If desired, a suitable inert gas, e.g., nitrogen, can also be charged to the reaction zone to reduce the partial pressures of the reacted gases, i.e., hydrogen and carbon monoxide.

The relative concentration of the carbon monoxide and hydrogen significantly affects the distribution of the normal and branched chain isomers in the product. The carbon monoxide to hydrogen ratio can be maintained from aobut 1:10 to about 1:3 and preferably from about 1:10 to about 1:5 to favor production of the straight chain aldehyde. Surprisingly, under these high hydrogen partial pressures the straight chain product can be obtained in amounts from 3 to 8 times the yield of the branched chain aldehyde.

The selectivity of the reaction for a straight chain aldehyde can also be increased by including limited amounts, e.g., 5–50 weight percent, of water in the reaction zone. The practice of the invention under substantially anhydrous conditions with about equal molar quantities of carbon monoxide and hydrogen produces about twice as much of the straight chain aldehyde as the branched chain aldehyde. The addition of water to this reaction in amounts from up to about 50 percent of the liquid reactants can increase the yield of normal up to about 4.2 times the yield of branched chain aldehyde. The aforementioned increase in hydrogen concentration, relative to carbon monoxide, can also be performed in the partially aqueous solvent to obtain even greater yields of the straight chain product. Preferably water from 5 to about 30 weight percent of the liquid reactants is used, the maximum water content being limited to maintain a soluble medium for the catalyst and the ethylenically unsaturated hydrocarbon.

The process can be conducted continuously or batchwise; however, the continuous processing is preferred. In the latter preferred technique, the catalyst is charged to the reaction zone in a suitable solvent or in excess of the unsaturated hydrocarbon and the gaseous reactants are introduced into contact with the reaction solvent and catalyst in the reaction zone. A continuous withdrawal of the liquid phase in the reaction zone can be employed; this material is then reduced in pressure to remove the dissolved gases which can be recycled, cooled and then distilled to recover the desired products. When low molecular weight products are produced, e.g., propionaldehyde, this product can be recovered by employing a high gas rate through the reactor to strip the product from the reaction solvent which, desirably, is a higher boiling liquid such as tertiary butanol, tertiary amyl alcohol, butyrolactone, etc.

Because the reaction conditions are very mild, the products can remain in the reaction zone without encountering undue degradation to less desired products and therefore batchwise operation can be practiced by introducing the olefin, hydrogen and carbon monoxide into contact with the catalyst solution until a sufficient inventory of product is accumulated in the reaction zone and thereafter the reaction discontinued and the product recovered by suitable steps, typically distillation.

In the presence of the bicyclo or tricyclo(heterocyclo) amine of our invention, however, we have discovered that not only is the reaction rate accelerated, but the nature of the product is altered in favor of the straight-chain aldehydes.

The practice of the invention will now be illustrated by the following Examples 1–9, which will also serve to demonstrate the results obtainable thereby and by Example 10 which compares the results obtained in the absence of the invention with those in the presence of the invention.

EXAMPLE 1

The carbonylation of ehtylene was practiced by introducing into a one-gallon titanium lined autoclave 300 grams methanol containing 1 gram rhodium chloride and 4 grams of 1,4-diazabicyclo (2.2.2)octane. The autoclave was closed, purged with carbon monoxide and pressured to 14 atmospheres absolute with ethylene, then to 35 atmospheres with carbon monoxide and finally to 55 atmospheres with hydrogen. The autoclave was then heated to 107° C. and maintained at that temperature for a period of 60 minutes. The autoclave was then cooled, depressured, opened and the liquid contents weighed to determine that a 65 gram weight increase had occurred. The liquid contents were distilled to recover 4.8 grams propionaldehyde and 54.5 grams of 1,1-dimethoxy propane. During the distillation a slight precipitation of rhodium from the solution was observed.

EXAMPLE 2

Example 1 was repeated with substitution of 350 grams butyrolactone as the reaction solvent. The autoclave was pressured to 14 atmospheres with ethylene, to 25 atmospheres with carbon monoxide and finally to 35 atmospheres with hydrogen. After a 60 minute reaction time at 100° C., the product was found to comprise 64.6 grams of propionaldehyde.

The reaction was again repeated with substitution of 300 grams t-butyl alcohol as the reaction solvent. The autoclave was pressured to 14 atmospheres with ethylene, to 35 atmospheres with carbon monoxide and finally to 55 atmospheres with hydrogen. After a 30 minute reaction period at 107° C., the autoclave was opened and the liquid contents weighed to determine that a 43 gram weight increase had occurred. Distillation of the crude reaction product yielded 38.4 grams of propionaldehyde. A slight precipitation of the catalyst was observed during the distillation.

The reaction was repeated by introducing 300 grams tertiary butyl alcohol containing 1 gram rhodium chloride, 4 grams of 1,4-diazabicyclo(2.2.2)octane and 4 grams triphenylphosphine into the autoclave. The autoclave was closed and pressured to 14 atmospheres with ethylene, to 35 atmospheres with carbon monoxide and finally to 55 atmospheres with hydrogen. After a 15 minute reaction period at 107° C., the autoclave was cooled, depressured and opened and the liquid contents weighed to determine that an 82 gram weight increase had occurred. The liquid product was distilled to recover 85.5 grams of propionaldehyde. No precipitation of rhodium metal occurred in the reaction or during the distillation. This experiment demonstrated that the biphyllic ligand additive stabilized the catalyst and greatly increased the rate of reaction.

EXAMPLE 3

To determine the reactivity of propylene, the autoclave was charged with 300 grams tertiary butyl alcohol, 1 gram rhodium chloride and 6 grams of 1,4-diazabicyclo(2.2.2)octane. The autoclave was closed, purged with nitrogen, charged with 105 grams propylene and then carbon monoxide was introduced to raise the pressure 10 atmospheres followed by an additional 10 atmosphere increase with hydrogen. The autoclave was then heated to 107° C. and maintained at that temperature for a period of 90-minutes. Upon completion of the reaction period the autoclave was cooled, depressured and opened and the liquid contents weighed to determine that a 5 gram weight increase had occurred. The products were distilled to recover 5 grams normal butyraldehyde and 5.6 grams isobutyraldehyde. No other detectable by-products were found and some precipitation of the catalyst was observed during distillation.

The reaction was repeated with the substitution of 300 grams tertiary amyl alcohol for the tertiary butanol perviously employed and 4 grams triphenyl phosphine was included in the catalyst mixture. The autoclave was charged with 135 grams propylene purged with nitrogen and pressured 20 atmospheres with carbon monoxide and an additional 20 atmospheres with hydrogen. The autoclave was heated to 88° C. and maintained at that temperature for 60 minutes. Upon completion of the reaction period the autoclave was cooled, depressured and opened and its contents weighed to determine that a 65 gram weight increase occurred. The products were distilled to recover 33.5 grams normal butyraldehyde and 13.7 grams isobutyraldehyde.

The autoclave was charged with 300 grams t-butyl alcohol, 0.4 gram rhodium chloride, 2 grams triphenyl phosphine and 2 grams 1,3,5,7-tetrazatricyclo(3.3.1)decane. The autoclave was closed, purged with nitrogen and charged with 132 grams propylene. Carbon monoxide was admitted to raise the autoclave pressure 20 atmospheres and then an additional 20 atmospheres with hydrogen. The autoclave was heated to 88° C. and maintained at that temperature for 60 minutes. The reaction product was distilled to recover 8.6 grams normal and 3.8 grams isobutyraldehyde.

EXAMPLE 4

Into a ½ gallon autoclave was charged 250 grams t-butyl alcohol, 2.0 grams 1,4-diazabicyclo(2.2.2)octane, 2.0 grams triphenylphosphine and 0.5 gram iridium chloride. The autoclave was closed, pressured to 21 atmospheres with ethylene, 42 atmospheres with carbon monoxide and 62 atmospheres with hydrogen. The autoclave contents were heated to 130° C. and held at that temperature for 1½ hours. The autoclave was cooled, depressured and opened and the liquid contents distilled to 43 grams of propionaldehyde.

EXAMPLE 5

The ½ gallon autoclave was charged with 250 grams t-amyl alcohol, 2 grams 1,4-diazabicyclo(2.2.2)octane, 2 grams ethylene bis(diphenyl phosphine) and 0.4 gram rhodium chloride. The autoclave was closed, purged with nitrogen and then charged with 120 grams propylene. Carbon monoxide was introduced to raise the autoclave pressure 20 atmospheres and then hydrogen was introduced to raise the pressure an additional 20 atmospheres to about 50 atmospheres. The autoclave was heated to and maintained at 88° C. and maintained at that temperature for about 1 hour. The autoclave was then cooled, depressured and opened and the liquid contents weighed to indicate a 46 gram increase. A sample of the product analyzed by gas chromatography revealed that a mixture of butyraldehydes was produced having a ratio of the normal to the isomer of 1.6.

The autoclave was charged with 300 grams t-butyl alcohol, 0.4 gram rhodium chloride, 4 grams 1,4-diazabicyclo(2.2.2)octane and 3 grams tri-o-tolylphosphine. The autoclave was closed, purged with nitrogen and 98 grams of propylene were added. Thereafter carbon monoxide, then hydrogen, were charged to the autoclave to raise its pressure 20 atmospheres with addition of each reactant. The autoclave was heated to 88° C. and maintained at that temperature for 60 minutes. The crude product was distilled to recover 20.5 grams normal and 16.3 grams isobutyraldehyde.

EXAMPLE 6

The following series of experiments illustrate the effect of varied carbon monoxide/hydrogen ratios of the product distribution. The ½ gallon autoclave was charged with 250 grams butyrolactone, 2 grams 1,4-diazabicyclo(2.2.2)octane, 2 grams triphenylphosphine, 0.3 gram rhodium chloride. The autoclave was closed, purged with nitrogen and 132 grams propylene were introduced. Carbon monoxide was then introduced to raise the autoclave pressure by 20 atmospheres and then an additional 21 atmospheres increase with hydrogen. The autoclave was heated to 91°–96° C. and maintained at that temperature for 8 minutes. The autoclave was then cooled, depressured and opened and the liquid contents distilled to recover 104 grams of mixed butyraldehydes having a ratio of the normal to the isomer of 2.5.

The experiment was repeated; however, the autoclave was pressured with only 11 atmospheres of carbon monoxide and 37 atmospheres (total pressure about 48 atmospheres) with hydrogen. After 15 minutes at 190° F. the autoclave was cooled and the contents distilled to recover 53 grams mixed butyraldehydes having a ratio of the normal to the isomer of 3.7.

The experiment was again repeated; however, the autoclave was pressured only 8 atmospheres with carbon monoxide and 35 atmospheres (total pressure about 43 atmospheres) with hydrogen. A total of 17 grams mixed butyraldehydes was obtained within a 20-minute reaction period at 85°–88° C. with a ratio of the normal to the branched chain aldehyde of 8.0.

EXAMPLE 7

The following experiments illustrate the effect of water on the reaction rate and product distribution. Into a ½ gallon autoclave was charged 300 grams butyrolactone, 50 grams water, 2 grams, 1,4-diazabicyclo(2.2.-2)octane, 2 grams triphenylphosphine and 0.4 gram rhodium chloride. The autoclave was closed, purged with nitrogen and 104 grams of propylene were introduced. Thereafter equal volumes of carbon monoxide followed by hydrogen were introduced to raise the pressure 42 atmospheres. The autoclave was heated to 88° C. and maintained at that temperature for 6 minutes, then cooled, depressured and opened. The liquid products were distilled to obtain 90.5 grams normal butyraldehyde and 21.7 grams isobutyraldehyde(ratio of 4.17).

The experiment was repeated; however, the water content was increased to 87 grams and the butyrolactone content was decreased to 263 grams. The following products were obtained within a 6 minute reaction period at 88° C.: 96.3 grams normal butyraldehyde and 20.4 grams isobutyraldehyde (ratio of normal to iso of 4.23).

The experiment was repeated substituting 35 grams water and 315 grams butyrolactone for the previously empolyed solvent. The following products were obtained within a 6 minute reaction period at 88° C.: 90.0 grams normal butyraldehyde and 25.1 grams isobutyraldehyde (ratio of normal to iso of 3.6).

EXAMPLE 8

A mixture of 300 grams t-amyl alcohol, 2 grams 1,4-diazabicyclo(2.2.2)octane, 2 grams triphenylphosphine and 0.4 gram rhodium chloride was charged to a ½ gallon autoclave. The autoclave was closed, purged with nitrogen and 132 grams 1-butene were added and then equal volumes of carbon monoxide followed by hydrogen were introduced to raise the pressure 40 atmospheres. The autoclave was heated to 88° C. and maintained at that temperature for 1 hour. The autoclave was then cooled, depressured, opened and the liquid contents distilled to recover 23.3 grams normal valeraldehyde and 7.3 grams 2-methylbutanol (ratio of normal to iso of 3.2).

The experiment was repeated with 135 grams 2-butene. After reaction for 1 hour at 88° C., 2.1 grams 2-methylbutanol were obtained.

The experiment was repeated with 100 grams 1-hexene. After reaction for 15 minutes at 88° C., the following products were obtained: 62.1 grams normal heptanal and 20.0 grams 2-methylhexanal (ratio, normal to iso of 3.11).

A mixture of 250 grams butyrolactone, 2 grams 1,4-diazabicyclo(2.2.2)octane, 2 grams triphenylphosphine and 0.3 grams rhodium trichloride was charged to a ½ gallon autoclave. The autoclave was closed, purged with nitrogen and 100 grams of allylbenzene were added. The autoclave was pressured with sufficient carbon monoxide to raise the pressure 20 atmospheres and then with sufficient hydrogen to raise the pressure another 20 atmospheres. The autoclave was heated to 104° C. and maintained at tht temperature for 10 minutes, then cooled, depressured and opened. The liquid contents were distilled to recover 95 grams of a mixture of 4-phenylbutyraldehyde and 3-phenyl-2-methyl propionaldehyde having a weight ratio of 1.9 of the former to the latter product.

EXAMPLE 9

The ½ gallon autoclave was charged with a mixture of 250 grams butyrolactone, 2 grams 1,4-diazabicyclo(2.2.2)octane, 2.6 grams triphenylstibine and 0.3 gram rhodium trichloride. The autoclave was closed, purged with nitrogen and 177 grams propylene were introduced followed by sufficient carbon monoxide to raise the pressure 20 atmospheres and then by sufficient hydrogen to raise the pressure another 20 atmospheres. The autoclave was heated to 88° C. and maintained at that temperature for 2 hours, then cooled, depressured and opened. The liquid contents were distilled to recover 32 grams of butyraldehydes having a weight ratio of the normal to the branched-chain aldehyde of 1.8.

The experiment was repeated; however, 2.3 grams triphenylarsine were substituted for the stibine previously used. The autoclave was charged with 120 grams propylene, heated to 127° C. and maintained at that temperature for 65 minutes; other conditions duplicating those of the preceding experiment. The product was distilled to recover 48 grams of butyraldehydes with a weight ratio of normal to the branched-chain aldehyde of 1.3.

EXAMPLE 10

This example demonstrates the results obtained in the absence of the invention with those obtained in the presence of a typical amine of the invention. The first 5 experiments demonstrate the results obtained in the absence of any amine and in the presence of the amines of the prior art. The last experiment demonstrates the greatly improved results utilizing a typical amine of the invention.

Into a 1-gallon titanium lined autoclave were introduced 300 grams methanol and 1 gram rhodium chloride. The autoclave was closed, purged with carbon monoxide and pressured to 14 atmospheres ethylene, then to 35 atmospheres with carbon monoxide and finally to 55 atmospheres with hydrogen. The autoclave was then heated to 107° C. and maintained at that temperature for a period of 30 minutes. The autoclave was then cooled, depressured, opened and the liquid contents weighed. The contents were distilled to discover that essentially no propionaldehyde was formed.

The above experiment was repeated except that 4 grams of pyridine was included in the reaction medium. It was found that essentially no propionaldehyde was formed in the process.

Into the 1-gallon autoclave were added 300 grams of t-amyl alcohol, 0.4 gram rhodium trichloride, 6.6 grams of tri-n-butylamine, 4 grams triphenylphosphine and 106 grams propylene. The autoclave was closed, pressured to 21.5 atmospheres with carbon monoxide, pressured an additional 20 atmospheres with hydrogen, heated to 88° C. and maintained at that temperature with stirring for 60 minutes. Upon completion of the 60 minute period, the autoclave was cooled, depressured and opened and the liquid contents weighed to reveal an 8 gram weight increase. The liquid contents were distilled to recover 6.1 grams normal butyraldehyde and 3.1 grams isobutyraldehyde and a distillation residue containing a yellow precipitate.

Into the autoclave were added 300 grams t-amyl alcohol, 0.4 gram rhodium trichloride, 2 grams triphenylphosphine, 3 grams pyridine and 124 grams propylene. The autoclave was closed, pressured to 21.5 atmospheres with carbon monoxide, an additional 20 atmospheres with hydrogen, heated to 88° C. and maintained at that temperature with stirring for 60 minutes. Essentially no reaction occurred during the 60 minute period and no essentially hydroformylation products were formed. The liquid contents upon completion of the reaction period contained a yellow precipitate.

The following experiment represents the results obtained in the presence of a typical bicyclo(heterocyclo)amine of the invention.

To the autoclave were added 300 grams t-amyl alcohol, 0.4 gram rhodium trichloride, 1 gram of 1-4-diazabicyclo(2.2.2)octane, 4 grams triphenylphosphine and 115 grams of propylene. The autoclave was closed and pressured 21.5 atmospheres with carbon monoxide and an additional 20 atmospheres with hydrogen. The autoclave was heated to 88° C. and maintained at the temperature 15 minutes with stirring, then cooled, opened and the liquid contents weighed to reveal an 83 gram weight increase. Distillation of the liquid contents produced 58 grams normal butyraldehyde and 30.9 grams isobutyraldehyde.

The above results indicate that the bicyclo(heterocyclo)amine having a nitrogen in a bridgehead position greatly increased the yield of the aldehyde product.

It may be seen that when triazabicyclo(1.1.1) pentane, 1,5,6-triazabicyclo(2.1.1)hexane, 1,7-diazabicyclo(2.2.1)heptane, 1,3,5-triazabicyclo(2.2.1)heptane, 1,7-diazatricyclo(3.3.1.2) undecane, 3-thia-1,7-diazabicyclo(3.2.1)octane and 1,6-diazatricyclo(5.3.1.1)dodecane are each substituted in approximate equal molar quantity for the (heterocyclo) saturated amines illustrated in the above experiments, that similar results are obtainable.

I claim:

1. In a method for the hydroformylation of an olefin by adding carbon monoxide and hydrogen to the olefin, reacting said mixture in the presence of a hydroformylation catalyst and recovering the aldehyde product, the improvement which comprises conducting the reaction in the presence of a complex catalyst consisting essentially of rhodium and triethylenediamine the molar ratio of triethylenediamine to rhodium metal being within the range of from 0.023 to 2280.

2. The method of claim 1 wherein a reaction residue containing the complex catalyst is recovered and recycled to the hydroformylation reaction.

* * * * *

UNITED STATES PATENT AND TRADEMARK OFFICE
CERTIFICATE OF CORRECTION

PATENT NO. : 4,110,404
DATED : August 29, 1978
INVENTOR(S) : William D. Schaeffer It is certified that error appears in the above-identified patent and that said Letters Patent are hereby corrected as shown below:

On the cover page, at column 1, the list of inventors (Item [75]), "William D. Schaeffer, Pomona; Frank B. Booth, Placentia, both of California" should be -- William D. Schaeffer, Pomona, California -- ;

at column 1, line 67, "tht" should be -- that -- ;

at column 5, line 62, "Of-these" should be -- Of these -- ; and at column 10, line 38, "2 grams," should be -- 2 grams -- .

Signed and Sealed this

Thirtieth Day of October 1984

[SEAL]

Attest:

GERALD J. MOSSINGHOFF

Attesting Officer   Commissioner of Patents and Trademarks